(12) United States Patent
Fornasiero et al.

(10) Patent No.: US 9,035,555 B2
(45) Date of Patent: May 19, 2015

(54) MEDICAL LIGHTING DEVICE AND PROCESS FOR OPERATING A MEDICAL LIGHTING DEVICE

(75) Inventors: Livio Fornasiero, Bliestorf (DE); Maral Haar, Hamburg (DE)

(73) Assignee: Dräger Medical GmbH, Lübeck (DE)

( * ) Notice: Subject to any disclaimer, the term of this patent is extended or adjusted under 35 U.S.C. 154(b) by 908 days.

(21) Appl. No.: 13/242,575

(22) Filed: Sep. 23, 2011

(65) Prior Publication Data

US 2012/0161647 A1 Jun. 28, 2012

(30) Foreign Application Priority Data

Dec. 22, 2010 (DE) .......................... 10 2010 055 666

(51) Int. Cl.
*H05B 37/02* (2006.01)
*H05B 33/08* (2006.01)
*A61B 19/00* (2006.01)

(52) U.S. Cl.
CPC ........ *H05B 33/0857* (2013.01); *A61B 19/5202* (2013.01); *A61B 2019/461* (2013.01); *A61B 2019/467* (2013.01)

(58) Field of Classification Search
CPC ..... F21V 23/0435; F21V 19/02; F21V 21/02; H05B 37/02; H05B 37/029; H05B 33/0812; H05B 33/0857; H05B 33/0863; H05B 37/0245; H05B 37/0272; H05B 39/088
USPC ......... 315/149–159, 307, 308, 295, 129, 133; 362/33, 84, 109, 227–241, 804
See application file for complete search history.

(56) References Cited

U.S. PATENT DOCUMENTS

| 4,316,237 | A |   | 2/1982  | Yamada et al. |
| 4,989,466 | A | * | 2/1991  | Goodman ...................... 74/5.22 |
| 5,383,105 | A |   | 1/1995  | Agut |
| 5,526,245 | A | * | 6/1996  | Davis et al. ................... 362/233 |
| 6,803,727 | B2 |  | 10/2004 | Laerum et al. |

(Continued)

FOREIGN PATENT DOCUMENTS

| DE | 3227494 A1    | 2/1984 |
| DE | 200 15 892 U1 | 1/2001 |
| DE | 203 16 755 U1 | 3/2005 |
| DE | 102004055838 A1 | 6/2006 |

(Continued)

*Primary Examiner* — Douglas W Owens
*Assistant Examiner* — Amy Yang
(74) *Attorney, Agent, or Firm* — McGlew and Tuttle, P.C.

(57) ABSTRACT

A medical lighting device has an operating area light (100), a central control station (11), a lighting control unit (7), a control unit (39), an image detection element (27), an image processing unit (29), reference elements (67, 69), an operating unit (200), a position sensor (25), an operating element (33) arranged at a handle (31), a marking and distance detection element (35) and a device for data transmission (13, 15, 17, 19, 21, 26, 28). A horizontal-vertical position (58) of the operating unit (200) in the room and a light marking position (38) on a reclining surface (99) are determined by the position sensor (25), the marking and distance detection element (35), the image detection element (27) combined with reference elements (67, 69) and image processing unit (29). The operating area light (100) is actuated such that an illuminated area (71) is illuminated on the reclining surface.

13 Claims, 4 Drawing Sheets

(56) References Cited

U.S. PATENT DOCUMENTS

| | | | |
|---|---|---|---|
| 7,441,923 B2 | 10/2008 | Huenerbein et al. | |
| 2005/0180615 A1* | 8/2005 | Gerder | 382/124 |
| 2007/0014567 A1 | 1/2007 | Rossner et al. | |
| 2008/0068852 A1* | 3/2008 | Goihl | 362/509 |
| 2008/0290818 A1* | 11/2008 | Fontijn | 315/295 |
| 2009/0261759 A1 | 10/2009 | Fornasiero | |
| 2010/0238271 A1* | 9/2010 | Pfeiffer et al. | 348/46 |
| 2012/0206050 A1* | 8/2012 | Spero | 315/152 |

FOREIGN PATENT DOCUMENTS

| | | | |
|---|---|---|---|
| DE | 102007002382 A1 | 7/2008 | |
| EP | 1 084 364 B1 | 9/2006 | |
| WO | 02/16824 A1 | 2/2002 | |
| WO | WO 0216824 A1 * | 2/2002 | |
| WO | WO 2008097114 A1 * | 8/2008 | H05B 37/02 |

* cited by examiner

MEDICAL LIGHTING DEVICE AND PROCESS FOR OPERATING A MEDICAL LIGHTING DEVICE

CROSS REFERENCE TO RELATED APPLICATIONS

This application claims the benefit of priority under 35 U.S.C. §119 of German Patent Application DE 10 2010 055 666.1 filed Dec. 22, 2010, the entire contents of which are incorporated herein by reference.

FIELD OF THE INVENTION

The present invention pertains to a medical lighting device and to a process for operating a medical lighting device.

BACKGROUND OF THE INVENTION

The medical lighting device comprises an operating unit and an operating area light. The operating area light is arranged above an operating area on the ceiling of an operating room. At least one lighting module with at least one controllable light source each is arranged for this in the operating area light. An operating unit makes it possible to actuate the at least one light source of the operating area light. A handle, at least one operating element, a position sensor and a marking and distance detection element for setting an illuminated area on the operating area are arranged for this at the operating unit. Furthermore, at least one image detection element with an image processing unit is provided in order to determine, in cooperation with at least two reference elements arranged at a predetermined distance from each other, the positions in space of the operating unit and/or the handle in the vertical and horizontal directions in relation to the room ceiling and to the operating area. In addition, a central control station for coordinating the lighting device according to the present invention and a lighting control unit connected to the central control station for actuating the at least one light source of the operating area light are provided. The central control station is connected to the operating unit and to the operating area light via wired or wireless data connections. Remote control of the operating area light can be performed by means of the operating unit.

US 2007 014 567 A discloses a combination of an operating light and an image detection means, wherein the operating light is suspended in a mobile and movable manner on a bracket and a camera is provided, which is in a known or detectable orientation in space in relation to the operating light. The signals of the camera are analyzed in order to rotate or move the operating light such that a shadow-free illumination is given.

US 2008 290 818 A describes a process for directing a plurality of spotlights in terms of the intensity of illumination, light color and radiation direction onto a predefined illuminated area. A sensor element is provided for this, which is placed in the illuminated area in order to detect the illumination situation and to actuate the corresponding spotlights in a remotely controlled manner. The sensor element is capable of distinguishing the individual spotlights from each other, because each spotlight sends a characteristic additional light signal, which is superimposed to the light beam proper. The drawback of this process is that a sensor must be placed in the illuminated area to carry out the process and the spotlights must be provided with the additional characteristic light signal. Placing sensors in the illuminated area, possibly even on the body of a patient, is not practicable in the overwhelming majority of applications in the clinical practice of an operating room.

DE 10 2007 002 382 A discloses a lighting arrangement with a light source for illuminating a surface with light of variable properties, in which a control means for controlling the property of the light is provided, which is connected to a sensor and is set up to determine from the output signals of the sensor lighting values of at least one partial segment of the surface, to compare the lighting values determined with a predefined lighting value and to generate, as a function of the comparison, control signals, with which the light source is actuated to correct the property of the light. Furthermore, a lighting process is presented. The illumination situation of the surface is detected by means of the sensor. The drawback of this arrangement is, on the one hand, that only a part of the illuminated surface can be detected by means of the sensor, and, on the other hand, arrangement of the sensor leads to a limitation of the access to the patient and additionally also causes the casting of a shadow onto the illuminated surface. Such a casting of a shadow by operating elements or equipment is to be avoided in the practice of an operating room as much as possible.

DE 32 27 494 describes an operating light device, whose light beam is automatically adjusted to the position of the dentist's chair such the treating light always remains directed onto the area of the patient's mouth.

U.S. Pat. No. 6,803,727 B3 describes a lighting system with a lighting means, wherein the lighting means can be moved by a control in the X-Y direction so as to illuminate an area. The area is adjusted in this case into a focal area, and the focal area is defined by an optical, ultrasound- or radio frequency-based pointer device. Signals of the pointer device are received by suitable receiving means arranged in the room and sent to the control. The illuminated area and the focal area of the lighting system are selected in a remotely controlled manner by means of an opening and control unit connected to the control or by means of the pointer device. Lighting means are selected in a remotely controlled manner by means of operating elements, which are arranged at the operating and control unit and the brightness and focus of said lighting means are set in an indirect manner by means of drive elements. One advantage of a lighting system according to U.S. Pat. No. 6,803,727 B3 is that optimal setting of the light on the operating area can be achieved with an arrangement of a plurality of actuatable lighting elements compared to an individual operating light in the room on the ceiling. The drawback of this setting of the lighting is that the operating and control unit is necessary in addition to the pointer device for selecting the lighting parameters and the illuminated area and the operation by means of the operating unit is markedly different from the usual operation of an individual operating light. Operation by means of an operating and control unit requires inputs and continuous corrections during a surgical operation, and the clinical staff usually must temporarily leave the operating table to perform these tasks in order to make the settings. This leads to a compromise of the activities proper of the clinical staff at the operating table and can be compensated by additional staff only, which staff would have to be kept available for operating the lighting control away from the operating room.

US 2009 261 759 A describes a device and a process for uniformly illuminating an operating area. An operating area of interest is selected in this case by means of a control unit, the illumination situation of the operating area is detected by a camera, and individual lighting elements of a lighting unit are switched such that a shadow-free illumination of the lighted area of interest is obtained. The selection of the lighted field of interest requires initializations and inputs by the clinical operating staff before and during the performance of the surgical operation, for which the clinical staff must leave the area of the operating table at least temporarily. This leads to a burden for the clinical staff and can be compensated only by additional staff, which would have to be kept available for operating the lighting control away from the operating table.

In many cases in clinical practice, the use of a lighting system according to U.S. Pat. No. 6,803,727 B3 or the use of devices and processes for uniformly illuminating an operating area according to US 2009 261 759 A require changes at least partly in the routines and work processes during surgical operations, which cannot be implemented and are not practicable in every clinical situation.

Contrary hereto, the illuminated area can be set and the focus of the light beam or even the intensity of the light beam can be adjusted by a direct manual handling at the light itself, for example, by turning a handle in case of operating lights of a conventional design, which are arranged pivotably and rotatably on the ceiling or a ceiling-mounted support system.

Further operating lights of a conventional design are known from the state of the art in various embodiments, wherein DE 10 2004 055 838 A1, U.S. Pat. No. 7,441,923, U.S. Pat. No. 5,383,105, U.S. Pat. No. 4,316,237 and EP 1 084 364 describe embodiment variants that pertain specifically to the control of the lighting.

The drawback of conventional operating lights is that at least one additional, second operating light must be additionally used in many cases for setting a complex light situation for a special illumination situation, which often makes access to the patient difficult and makes handling difficult due to the movement and light settings of two operating lights in relation to one another.

SUMMARY OF THE INVENTION

The object of the present invention is therefore to provide a medical lighting device and a process for operating the medical lighting device, so that controlling of the lighting of the operating area is made possible with improved accessibility to the patient and with simplified handling.

The device according to the present invention comprises an operating area light, a central control station and an operating unit. The operating area light comprises at least one lighting module. The at least one lighting module comprises at least one controllable light source. The operating area light is preferably arranged above an operating area, and the operating area light is arranged in another preferred manner on the ceiling of an operating room.

The operating area comprises an operating table, as well as a space above the operating stable, as well as a space all around next to the operating table, which is needed for the clinical staff during the performance of the surgical operation for a reasonable freedom of movement.

Furthermore, a lighting control unit for actuating the lighting module and/or controllable light sources is provided next to the central control station. The central control station, operating unit and lighting control unit are connected to one another by means of wired or wireless data connections. The central control station and operating area light are connected to an electric power supply. The electric power supply of the operating unit may be wired by means of electric supply elements present in the operating room, but it is also possible to use batteries, for example, primary batteries or rechargeable batteries. Provisions are made in a preferred embodiment in case of using rechargeable batteries for at least one coupling station or a charging station to be arranged at the electric supply elements present in the operating room in order to plug in the operating unit and charge it with electric energy there. The charging of the rechargeable batteries of the operating unit in the at least one charging station may be carried out in an electric contact-connected or inductive contactless manner. Furthermore, besides the power supply, data transmission may take place between the operating unit and central control station via the coupling station in a contact-based, wired, optical or inductive contactless manner.

At least one operating element, a handle, a marking and distance detection element for optically marking an illuminated area and components for setting the current position of the operating unit in a room are arranged in or at the control unit.

The components for determining the position of the operating element in the room and/or for determining the position of the operating element in the operating area comprise a position sensor, which is designed to detect the slope of the operating unit in relation to the vertical, as well as a marking and distance detection element, which is designed, directed essentially downwardly in the vertical direction, to detect a distance between the operating unit and an operating table or a reclining surface, as well as at least two reference elements, which are arranged at a predetermined distance from each other, preferably on the ceiling of the room, and an image detection element with an image processing unit, which is designed, directed essentially upwardly in the vertical direction, to detect the at least two reference elements and thus to determine both a horizontal position of the operating unit in the room and a distance between the operating unit and the ceiling of the room. The position of the operating unit and the position of the operating unit in the room are determined by processing measured data of the at least one position sensor and of the marking and distance detection element, and measured data of the image detection element and of the image processing unit in the control unit. The image detection element is preferably designed as a camera or camera system and the marking and distance detection element is designed as an optical distance-measuring unit and, in another preferred manner, as a laser distance-measuring unit.

The position sensor is arranged in or at the operating unit and is designed to detect a deviation of the position of the operating unit from a vertical direction. The position sensor is preferably designed as a three-axis acceleration sensor, as an inclination sensor, for example, as a gyromagnetic sensor for detecting the magnetic field of the earth or as an inclinometric sensor for detecting the gravitational field of the earth. Further embodiment variants for the position sensor are capacitively measuring inclination sensors or inclination sensors measuring a heat flux or a shift in heat flux, so-called thermal inclination sensors, as well as also combinations of at least two mercury switches arranged at right angles in relation to one another. The position sensor is designed to make available measured data, which represent the orientation of the operating unit in a system of coordinates and indicate, moreover, a current angular position in relation to the vertical reference line. Cartesian coordinates, a system of polar coordinates or another system of coordinates suitable for the determination of a position and the description of a position may be used as a system of coordinates. The marking and distance detection element is designed to generate a light marking. The marking and distance detection element is designed, furthermore, to mark an illuminated area located in the vertical direction below the operating element on the reclining surface or on the operating table with the light marking and to detect a distance between the operating unit and the operating table or reclining surface. The marking and distance detection element is preferably designed as a distance-measuring instrument with a light pointer in the visible range of the light spectrum, and, in another preferred manner, it is designed as a laser distance-measuring instrument and is arranged, in another preferred manner, in or at the handle of the operating unit. To detect a horizontal position of the operating unit in the room, a vertical distance from the ceiling of the room is determined from the measured data of the image detection element and the image processor unit in the control unit and sent to the central control station.

To detect a vertical position of the operating unit above the operating table, a vertical distance from the marked, intended illuminated area on the operating table or reclining surface is determined from the measured data of the marking and distance detection element in the control unit. To detect the angular position, an angle $\phi$ to the vertical reference line $Y_0$ is determined from the measured data of the position sensor. In case the operating unit is oriented in parallel and at right angles to the vertical reference line, it is not necessary to take the angular position into account. Both the position of the operating unit in the room and the position of the illuminated area on the reclining surface or on the operating table are known from the angular position of the operating unit and the vertical position of the operating unit in relation to the ceiling of the room and to the operating table as well as from the horizontal position of the operating unit. The controllable light sources in the lighting modules are actuated via the data connections from the operating unit by means of the central control station to the lighting control unit such that the illuminated area selected and determined is lighted. The position sensor and system of coordinates of the position sensor are in a known relationship with the orientation of the position sensor in/at the operating unit, with the orientation of the image detection element in/at the operating unit and with the orientation of the marking and distance detection element at the operating unit, which relationship is preferably stored in the image processing unit and/or control unit, so that horizontal and vertical relative motions and angular inclinations of the operating unit in relation to the ceiling of the room and the operating room, as well as also a rotation of the operating unit about the central axis of the operating unit as a whole are imaged in a system of coordinates, which images both the position of the operating unit in the room and the position of the illuminated area on the reclining surface or on the operating table. Depending on the measuring technical specifications of the model of the position sensor used, the image data of the image detection element are used in the control unit to supplement the measured data of the position sensor for determining the vertical position of the operating unit in the room.

For example, a rotation of the operating unit about the central axis of the operating unit is also contained in the data of a three-axis acceleration sensor. When using an inclinometric sensor in an embodiment with, for example, only one axis to the gravitational field of the earth, the rotation of the operating unit about the central axis of the operating unit cannot be determined from the data of the inclinometric sensor alone, so that the rotation of the operating unit about the central axis of the operating unit must be included in a correcting manner in the angle determination of the vertical position of the operating unit in the room by supplementing with the image data of the image detection element.

In a special embodiment, the function of the position sensor may be fully or partly assumed by the image detection element and the image processing unit. Thus, it is possible, for example, if at least three reference elements are arranged on the ceiling of the room, the distances of the reference elements are known, at least three reference elements are arranged in the range of detection of the image detection element, and the three reference elements are arranged in a horizontal plane without a height offset in relation to one another, to calculate the angular position of the operating unit in the room from the image data with a high-resolution camera as an image detection element at the operating unit. For example, the angular position of the operating unit in the room, which angular position was determined by the position sensor, can be compared with the angular position of the operating unit in the room, which latter angular position was calculated from the image data, and a plausibility check can thus be performed. In order for there to be at least three reference elements in the range of detection of the image detection element, the image detection element is preferably designed as a camera with an extreme wide-angle lens, for example, with a "fisheye lens." The limits of the position determination by means of the image data are set essentially by the use of the wide-angle lens and the camera resolution and image noise of the camera. Two basic possibilities are thus obtained for the practical application; a position sensor may thus be eliminated in applications for room lighting, in which the angular accuracy of the operating unit is of lesser significance, and the angular position can be calculated from the image data, whereas the use of a position sensor is, by contrast, necessary for most applications in which the angular accuracy of the operating unit is of significance for a highly accurate illumination, and the angular position calculated by means of the image data can be used in a supplementary and optional manner for a plausibility check of the data of the position sensor or for calibrating the position sensor in the operating units for the conditions prevailing in the room.

In a preferred embodiment, a central position is stored by means of the operating element arranged at the operating unit. This central position designates the center of a predefined circle, whose circumference is indicated by the dimensions of the desired illuminated area.

At least two positions are stored in another preferred embodiment by means of the operating element arranged at the operating unit. These at least two positions designate the corner points of a predefined rectangle or a predefined ellipse, whose circumference is indicated by the dimensions of the desired illuminated area.

At least three positions are stored in another preferred embodiment by means of the operating element arranged at the operating unit. These at least three positions designate the corner points of a predefined rectangle, predefined triangle or predefined polygon, whose circumference is indicated by the dimensions of the desired illuminated area.

The reference elements are arranged in a preferred embodiment at the operating unit and the image detection elements and image processing unit are arranged on the ceiling of the room. A wireless data connection, for example, a radio data connection, is provided in another preferred embodiment between the operating unit and central control station in conjunction with an independent power supply of the operating unit, for example, by means of primary batteries or by means of rechargeable batteries, so that a mobile operating unit is obtained.

An orienting light source is arranged in another preferred embodiment at the operating unit, so that it is possible for the image detection elements in conjunction with the image processing unit to detect the position of the reference element on the ceiling of the room in a darkened environment as well.

An orienting light source is used in the room or on the ceiling of the room in an alternative preferred embodiment, so that it is possible for the image detection elements in conjunction with the image processing unit to detect the position of the reference elements at the operating unit in a darkened environment as well.

The orienting light source may be designed as a continuous light source, and the light source can be operated intermittently or switched on and off by triggering by the operating element in a special variant. The reference elements are preferably designed as reflecting elements, for example, as retroreflectors, also called reflectors or so-called "cat's eyes."

The marking and distance detection element is moved in terms of its position in the room by means of the handle arranged at the operating element in the process according to the present invention for operating a medical lighting device such that the intended illuminated area is marked by means of the light marking. Simultaneously and continuously herewith, the distance between the operating unit and reclining surface is continuously determined by the marking and distance detection element, and, furthermore, the distance between the operating unit and ceiling of the room and the horizontal position in the room are continuously determined by the image detection element and image processing unit, and, furthermore, the angle $\phi$ of the operating unit in relation to the vertical reference line $Y_0$ is determined likewise continuously by the position sensor. If necessary, data of the image processing unit are used during the determination of the angle $\phi$ to correct the angle $\phi$.

A horizontal-vertical position $P_{Oxyz}$ of the operating unit in the room, as well as a light marking position $PL_{xyz}$ on the reclining surface are determined, likewise continuously, from the horizontal position of the operating unit in the room, the vertical distances between the operating unit and the reclining surface and from the ceiling of the room, as well as from the angle $\phi$ of the operating unit relative to the vertical reference line, and, furthermore, an illuminated area is determined continuously from the light marking position $PL_{xyz}$ on the reclining surface, and coordinates of the illuminated area are determined and the operating area light is actuated such that the illuminated area determined is illuminated. The process according to the present invention will be described below in the form of a sequential succession of steps, wherein the steps can be carried out in the technical embodiment in the sequence of steps in a serial sequence as separate steps one after another. However, the present invention also covers the case in which the sequence of steps is carried out in another, selectable sequential order or even in a parallel and simultaneous manner, for example, in a multitasking system. Furthermore, other embodiments are comprised as well, which represent mixed forms from parallel and serial data processing and of status and valve polls and triggering of actions, for example, polling loops, interrupt and interrupt-service-request-based routines or master-slave bus communication in a manner in the sense of the present invention, as they are used, for example, in various measuring technical or industrial bus systems; the IEEE488 standard or the CAN BUS may be mentioned as examples herefor.

The continuous process with a sequence of seven steps begins immediately after switching on the medical lighting device and is ended by switching off the medical lighting device.

The position sensor is polled in a first step and an angle $\phi$ in relation to the vertical reference line is determined in a first step, the image detection element and image processing unit are polled and a horizontal position of the operating unit and a vertical distance of the operating unit from the ceiling of the room are determined in a second step, the marking and distance detection element is polled and a vertical distance from the reclining surface is determined in a third step, a three-dimensional position of the operating unit in the room is determined as a horizontal-vertical position $P_{Oxyz}$ from the two vertical distances determined, the horizontal position determined and the angle $\phi$ determined in a fourth step, and a three-dimensional position of the light marking on the reclining surface is determined as a light marking position $PL_{xyz}$, a status of the operating element is polled by the control unit in a fifth step and the light marking position $PL_{xyz}$ is updated as a function of the status of the operating element, coordinates of an illuminated area are determined from the light marking position $PL_{xyz}$ and made available as a coordinate data set in a sixth step, and a control data set is determined in a seventh step from the coordinate data set and the operating area light with the controllable light sources in the lighting modules is actuated such that illumination of the illuminated area determined on the reclining surface is given.

This sequence of steps is carried out continuously and, as it were, simultaneously after switching on the medical lighting device in a continual loop, and a new coordinate data set is generated in the fifth step each time the operating element is actuated, so that the illumination on the reclining surface will then always be updated.

Exemplary embodiments of the present invention will be explained in more detail below on the basis of drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
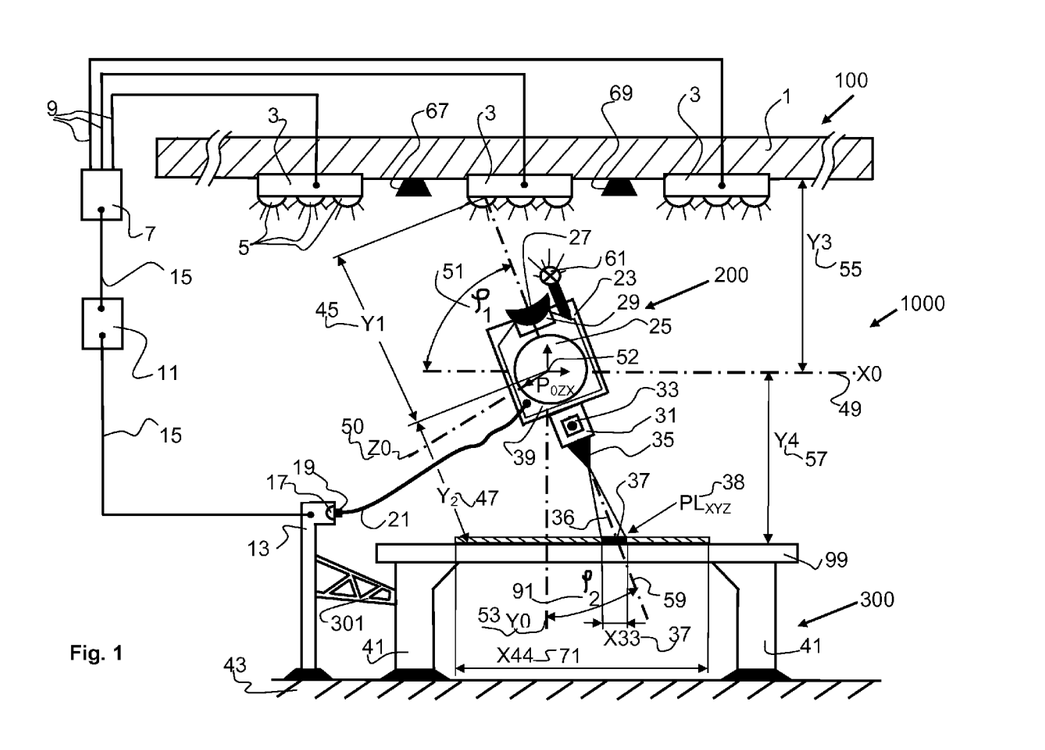
FIG. 1 is a two-dimensional schematic view showing an arrangement of a medical lighting device according to the intention.

Referring to the drawings in particular, FIG. 1 shows a two-dimensional view of an arrangement 1000 of an operating area light 100, an operating unit 200 and an operating table 300.

The arrangement is shown in a side view of an operating room with a ceiling 1 of a room and a floor 43 of a room. A first horizontal reference line $X_0$ 49, a second horizontal reference line $Z_0$ 50 and a vertical reference line $Y_0$ 53 represent a reference of an orientation in space of the arrangement of the operating area light 100, operating unit 200 and operating table 300. The operating area light 100 with lighting modules 3 and with controllable light sources 5 is arranged in/at the ceiling 1 of the room.

Figure 2:
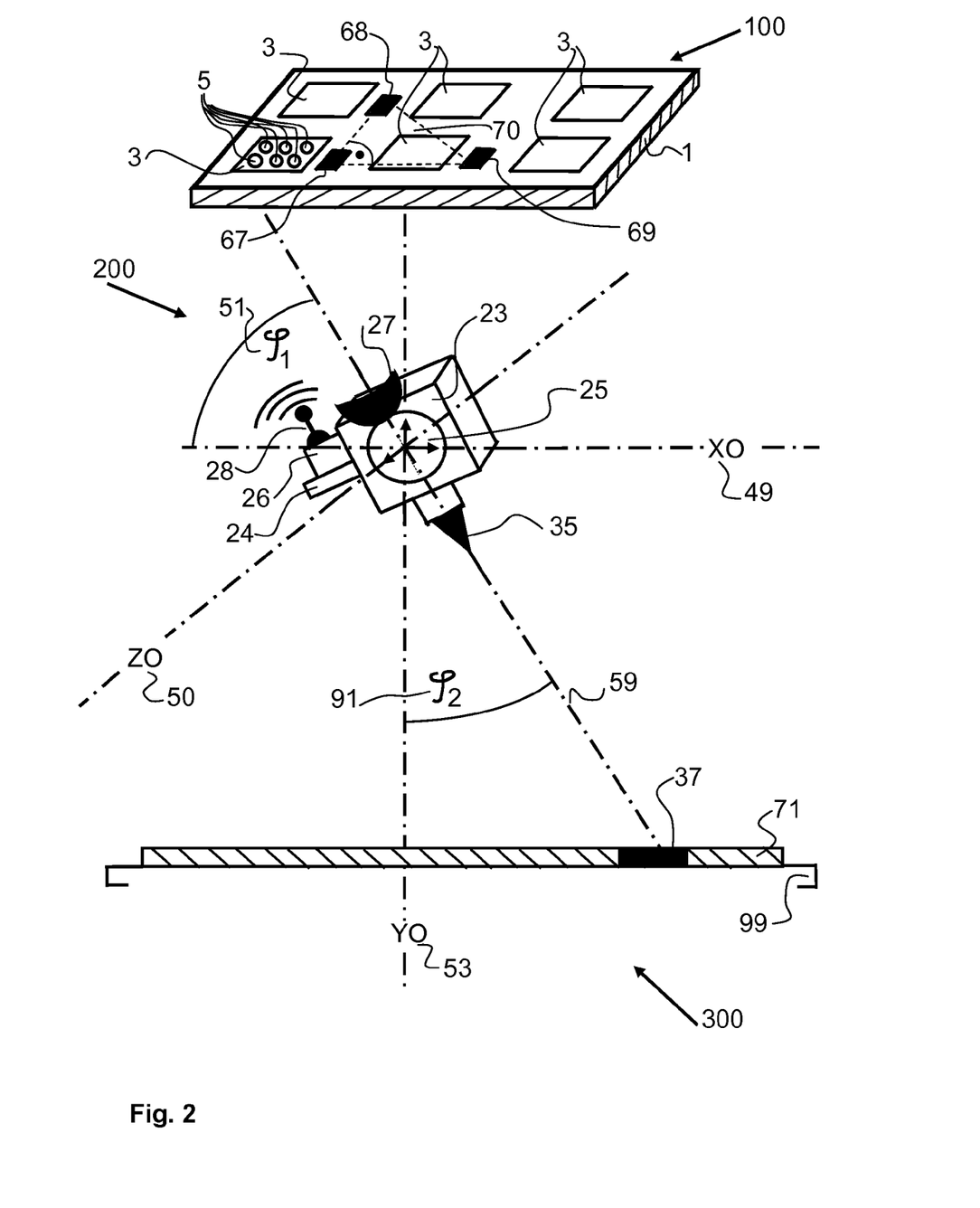
FIG. 2 is a simplified three-dimensional and partly expanded view of the arrangement of a medical lighting device according to FIG. 1.

At least a first and a second reference element 67, 69, as well as advantageously a third reference element 68 (not shown in this FIG. 1) are arranged on the ceiling 1 of the room. The three reference elements 67, 68, 69 are preferably arranged in relation to one another on the ceiling 1 of the room in the form of a right triangle 70 (FIG. 2) directed towards the horizontal reference lines $X_0$ 49 and $Z_0$ 50, wherein a reference element 67, 68, 69 (FIG. 2) is positioned at each corner of the triangle 70 (FIG. 2). The operating table 300 stands with a frame 41 and a reclining surface 99 on the floor 43 of the room. A coupling station 13 stands on the floor 43 of the room or/and is arranged at the frame 41 of the operating table 300 by means of a holding element 301. The horizontal reference lines $X_0$ 49 and $Z_0$ 50 are parallel to the ceiling 1 of the room and parallel to the floor 43 of the room, and the vertical reference line $Y_0$ 53 forms a right angle (90°) with the horizontal reference lines $X_0$ 49, $Z_0$ 50. The horizontal reference lines $X_0$ 49 and $Z_0$ 50 likewise form a right angle (90°). The lighting modules 3 are connected to a lighting control unit 7 via module control lines 9. A central control station 11 for controlling the operating area light 100 is provided. The central control station 11 is connected to the lighting control unit 7 and to the coupling station 13 via station control lines 15. The lighting control unit 7 may be designed in an alternative embodiment as a part of the central control station 11 or also comprised by the central control station 11. The coupling station 13 is connected to the operating unit 200 via a first and second coupling elements 17, 19 and via a data and supply cable 21. The first and second coupling elements 17, 19 are preferably designed as a plug-and-socket connection. The operating unit 200 comprises a housing 23, a handle 31 with an operating element 33, an image detection element 27, an image processing unit 29, a position sensor 25, a marking and distance detection element 35 and a control unit 39. The control unit 39 is designed to detect and process data of the operating element 33 as well as measured data and signals of the position sensor 25, image processing unit 29 and marking and distance detection element 35 and to send them via the data and supply cable 21 via the coupling station 13 and the station control lines 15 to the central control station 11.

To simplify the possibility of representation, the position sensor 25 lies in this view according to this FIG. 1 exactly in the intersection of the vertical reference line $Y_0$ 53 with the horizontal reference lines $X_0$ 49 and $Z_0$ 50. However, it is also possible for the position sensor 25 in the operating unit 200 with known distances from the reference lines $Y_0$ 53, $X_0$ 49, $Z_0$ 50 to be arranged outside the intersection of the three reference lines. The image detection element 27 and image processing unit are preferably embodied together with one another in an integrated camera module. The reference elements 67, 69 are arranged in the range of detection of the image detection element 27 at a predetermined and known distance from each other on the ceiling 1 of the room. In addition, an orienting light source 61 is arranged in the vicinity of the image detection element 27 in/at the operating unit 200. The reference elements 67, 69, 70 are designed to reflect light from the orienting light source 61 in the direction of the image detection element 27, so that this light can be detected by the image detection element 27. The image detected by the image detection element 27 is analyzed in the image processing unit 29 such that, including the predetermined and known positions of the reference elements 67, 68, 69, a first vertical distance $Y_1$ 45 is available on the ceiling 1 of the room in the control unit 39. Besides the first vertical distance $Y_1$ 45, a horizontal position $P_{Oxz}$ 52 of the operating unit in the room in relation to the first horizontal reference line $X_0$ 49 and in relation to the second horizontal reference line $Z_0$ 50 is determined from the detected image and the positions of the reference elements 67, 68, 69. The marking and distance detection element 35 is designed to image a light marking 37 on the reclining surface by means of an emitted light beam 36 and is designed, furthermore, to detect a second vertical distance $Y_2$ 47 from the reclining surface 99 of the operating table 300 and to make it available to the control unit 39. The light marking 37 generated by the marking and distance detection element 35 is preferably designed in the form of a circular or circle-like light spot. The light beam 36 may be designed as a diffuse light cone or as a focused ray beam.

The color temperature of the light beam 36 is preferably different from the color temperature of the room lighting in order to ensure good recognizability. In another preferred manner, the light beam may be reddish or greenish or bluish and/or such that a selection is possible between different preset light colors and/or shades. The position sensor 25 is designed to detect an orientation 59 of the operating unit 200 in relation to the reclining surface 99 of the operating table 300 by means of an angle measurement. Position sensor 25 is designed to detect a first angle $\phi_1$ 51, which corresponds to a tilting of the operating unit 200 in relation to the surface defined by the horizontal reference lines $X_0$ 49, $Z_0$ 50 in parallel to the ceiling 1 of the room and to the floor 43 of the room and/or a second angle $\phi_2$ 91, which corresponds to a tilting of the operating unit 200 in relation to the vertical reference line $Y_0$ 53. Due to the fact that the vertical and horizontal reference lines form a right angle with one another, it is sufficient in terms of the measuring technique to detect one of the angles $\phi_1$, $\phi_2$ 51, 91 and to determine the other by calculation. However, it may be useful or necessary, for example, for reasons of error correction, to measure both angles $\phi_1$, $\phi_2$ 51, 91 in order to be able to carry out a plausibility comparison. The data of the first vertical distance $Y_1$ 45 and of the second vertical distance $Y_2$ 47 are converted in the control unit 39 into a third vertical distance $Y_3$ 55 and a fourth vertical distance $Y_4$ 55, including the first and/or second angle $\phi_1$, $\phi_2$ 51, 91. Combined with the horizontal position $P_{Oxz}$ 52, the angles $\phi_1$, $\phi_2$ 51, 91, the first and second vertical distances $Y_3$ 55, $Y_4$ 57, the orientation 59 of the operating unit 200 is obtained as a horizontal-vertical position $P_{Oxyz}$ 58 of the operating unit 200 and likewise as a light marking position $PL_{xyz}$ 38 on the reclining surface 99. The horizontal-vertical position $P_{Oxyz}$ 58 of the operating unit 200 and the horizontal-vertical position of the light marking 37 are thus available in the central control station 11 as a light marking position $PL_{xyz}$ 38 in the room, as well as the position of the light marking position $PL_{xyz}$ 38 in relation to the horizontal-vertical position $P_{Oxyz}$ 58 of the operating unit 200. The control station 11 is designed to determine from the positions $PL_{xyz}$ 38 and $P_{Oxyz}$ 58 which lighting modules 3 and which controllable light sources 5 must be switched on or off in order to light up the surface marked by $PL_{xyz}$ 38 with light. In this embodiment according to this FIG. 1, the light marking 37 comprises a circular extension in space with a circle diameter $X_{33}$ 37. This circle diameter $X_{33}$ 37 represents in this embodiment the center of an illuminated area $X_{44}$ 71 on the reclining surface 99. The illuminated area $X_{44}$ 71 may advantageously likewise be obtained in this case as a circular area, for example, with a predetermined diameter ratio from the circle diameter $X_{33}$ 37 and the illuminated area $X_{44}$ 71, but the shape of the geometrically really illuminated surface is determined essentially by the arrangement of the lighting module 3 in the ceiling 1 of the room. The determination of the illuminated area $X_{44}$ 71 by the light marking $X_{33}$ 37 and the adjustment of the lighting modules 3 and controllable light sources 5 preferably take place in real time, i.e., the central control station 11 is designed such that it dynamically adjusts the switching on and off of the lighting modules 3 and of the controllable light sources 5 to a motion of the operating unit 200 in an adjustment mode without a considerable time delay. From this follows the advantage that the user moves, so to speak, a virtual operating light during the motion of the operating unit 200, with the difference that the light source itself is not an integral part of the operating unit 200 but is arranged as lighting modules 3 and a controllable light source 5 in the ceiling 1 of the room. The operating element 33 in the handle 31 of the operating unit 200 is designed to capture a position of $P_{0xyz}$ 58 of the operating unit 200 as a position information and thus to bring about at/in the central control station 11 a suspension of the adjustment of the lighting modules 3 and controllable light sources 5 and thus the static holding of an illumination situation with the illuminated area $X_{44}$ 71 in a holding mode. If a lighting situation is held, the user is able to couple the operating unit 200 to the coupling station 13. As a result, the operating unit 200 is outside the working area of the medical staff above the operating table 300 and thus it does not lead to any limitations, and, in addition, the operating unit 200 can be supplied with electric energy at the coupling station 13, as it is necessary, for example, in a special variant according to this FIG. 1 when the data and supply cable 21 is replaced by a communication module 26 (FIG. 2) with an antenna 28 (FIG. 2), designed as a wireless data transmission with the coupling station 13 or with the central control station 11, and the operating unit is operated by a power supply module 24 (FIG. 2) with rechargeable batteries. The operating element 33 may be designed to make it possible to switch over between the adjusting mode and holding mode. The operating element 33 may be additionally designed to switch a mode of operation with light focusing onto an illuminated area limited in space (spot mode) or a mode of operation with light focusing onto a wide illuminated area (room light mode). Furthermore, the size and shape of the illuminated area $X_{44}$ 71 can be defined in another mode of operation by the operating element 33, in which illuminated area a number of at least 2 points are marked one after another on the outer sides of the illuminated area $X_{44}$ 71, for example, instead of the selection of a center of the light marking $X_{33}$ 37 with a circular illuminated area $X_{44}$ 71 associated therewith in relation, in order to set a surface shape of the illuminated area $X_{44}$ 71. Such a surface shape may be, for example, rectangular or elliptical. The operating element 33 comprises in this case at least one individual button or individual switch or a group of button and/or switch elements for selecting the different modes of operation and operating states. In a special variant, the operating element 33 may be additionally provided with optical and/or acoustic signal generation in order to assist the user in the operation in order to indicate the operating steps, the mode of operation as well as the current state within a mode of operation or even to make an error message available. In another special manner, the light beam 36 may be designed for optical signal generation in such a way that, for example, the light color is permanently or briefly varied as a response to an input on the operating element 33 or in such a way that a variation is performed from a continuous visible light beam 36 into a form of a temporarily interrupted light beam 36, similarly to a Morse telegram code, or in a manner comparable to a code of sea marks.

FIG. 2 shows a simplified three-dimensional and partly expanded view of the arrangement according to FIG. 1, comprising an operating area light 100, an operating unit 200 and an operating table 300. Identical elements in FIG. 2 are designated by the same reference numbers as the identical elements in FIG. 1. The arrangement of the elements in this FIG. 2 corresponds largely to the arrangement of the elements in FIG. 1. A selection of elements corresponding to FIG. 1 is shown, the elements selected being especially those that are essential for the arrangement in space of the operating area light 100, operating unit 200 and operating table 300 in relation to one another and for the determination of the position of the operating unit 200 in the room. Unlike in FIG. 1, a power supply module 24 and a communication module 26 are arranged at the operating unit 200 in this FIG. 2. The communication module 26 is designed to exchange data with the central control station 11 (FIG. 1) via an antenna 28 in a wireless manner. Examples of wireless communication are radio data transmission systems and optical data transmission systems. A first horizontal reference line $X_0$ 49, a second horizontal reference line $Z_0$ 50 and a vertical reference line $Y_0$ 53 represent a reference for the orientation in space of the arrangement comprising the operating area light 100, operating unit 200 and operating table 300. The horizontal reference lines $X_0$ 49, $Z_0$ 50 are parallel to the ceiling 1 of the room and parallel to the illuminated area $X_{44}$ 71, and the vertical reference line $Y_0$ 53 forms a right angle each (90°) with the horizontal reference lines $X_0$ 49, $Z_0$ 50. The horizontal reference lines $X_0$ 49, $Z_0$ 50 likewise form a right angle (90°) with one another. A first and second reference elements 67, 69 as well as a third reference element 68 are arranged on the ceiling 1 of the room. The three reference elements 67, 68, 69 are arranged at a predetermined distance and angle in relation to one another. In the arrangement according to this FIG. 2, the connection lines between the two reference elements 67, 68 and the connection lines between the two reference elements 67, 69 are at a right angle (90°) in the form of a right triangle 70 in relation to one another. However, other angle combinations, for example, in the form of an equilateral or isosceles triangle 70, are also possible between the reference elements 67, 68, 69.

The determination of the positions $P_{0xz}$ 52 (FIG. 1), $P_{0xyz}$ 58 (FIG. 1) and $PL_{xyz}$ 38 (FIG. 1) with the cooperation of the position sensor 25, marking and distance detection element 35, control unit 39 (FIG. 1) as well as control of the lighting module 3 and the controllable light sources 5 in the ceiling 1 of the room by means of the lighting control unit 7 (FIG. 1) and central control station 11 (FIG. 1) is carried out as described in the description of FIG. 1.

Figure 3:
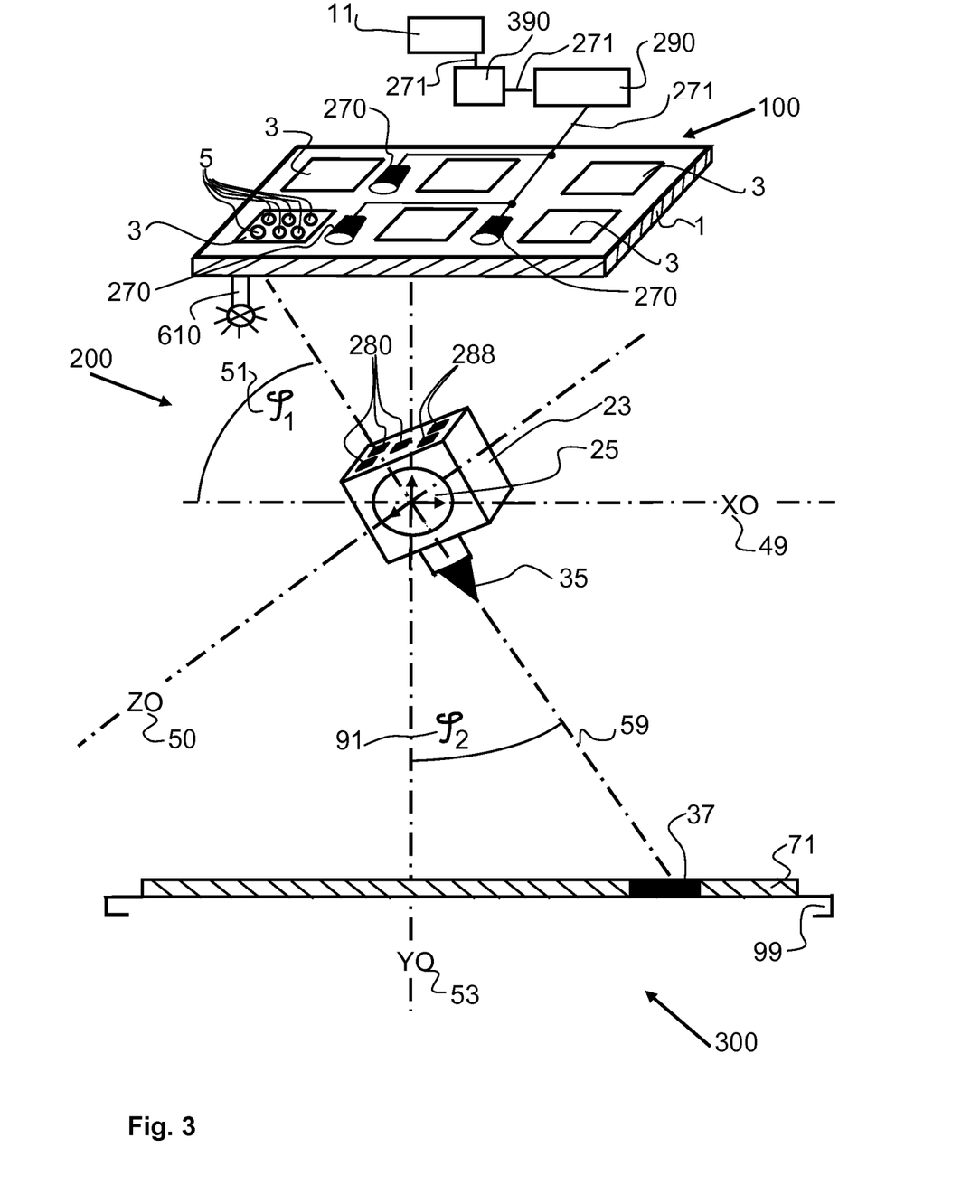
FIG. 3 is a simplified three-dimensional view of a second alternative arrangement of a medical lighting device according to the intention.

FIG. 3 shows a simplified three-dimensional view of an alternative arrangement comprising an operating area light 100, an operating unit 200 and an operating table 300. Identical elements in FIG. 3 are designated by the same reference numbers as the same elements in FIG. 1. A first horizontal reference line $X_0$ 49, a second horizontal reference line $Z_0$ 50 and a vertical reference line $Y_0$ 53 represent a reference for the orientation in space of the arrangement comprising the operating area light 100, operating unit 200 and operating table 300. The horizontal reference lines $X_0$ 49, $Z_0$ 50 are parallel to the ceiling 1 of the room and parallel to the illuminated area $X_{44}$ 71, and the vertical reference line $Y_0$ 53 forms a right angle (90°) each with the horizontal reference lines $X_0$ 49, $Z_0$ 50. The horizontal reference lines $X_0$ 49, $Z_0$ 50 likewise form a right angle (90°) each with one another. The arrangement of the elements in this FIG. 3 largely corresponds to the arrangement of the elements in FIG. 1. A selection of elements corresponding to FIG. 1 is shown, the elements selected being especially those that are essential for the arrangement in space of the operating area light 100, operating unit 200 and operating table 300 and for the determination of the operating unit 200 in the room. Contrary to FIG. 1 and FIG. 2, the arrangement of reference elements 67, 68, 69 (FIG. 2) and the image detection element 27 (FIG. 2) is transposed. An arrangement of at least one image detection element 270 in/at the ceiling 1 of the room is provided, which is connected to an image processing unit 290 via data lines 271. The image processing unit 290 is connected via additional data lines 271 to a control unit 390 and the central control station 11. An arrangement of at least two reference elements 288 and preferably three reference elements 280 is provided at the operating unit 200. Furthermore, an orienting light source 610 is arranged on the ceiling 1 of the room. The determination of the position of the operating unit 200 on the basis of the reference elements 280, 288, image detection elements 270 and image processing unit 290 is carried in a similar manner as described in the description of FIG. 1. The arrangement of three reference elements 280 makes possible the recognition of a tilting of the operating unit 200 in reference to the three reference lines $X_0$ 49, $Z_0$ 50, $Y_0$ 53, as well as the recognition of the rotation position of the operating unit 200 in reference to the orientation and orientation axis of the operating unit 200. The vertical distance of the operating unit 200 in the direction of the vertical reference line $Y_0$ 53 from the ceiling 1 of the room is determined by the at least one image detection element 270 and the image processing unit 290 on the basis of the arrangement of the reference elements 280, 288. Furthermore, the horizontal distances in the direction of the first horizontal reference line $X_0$ 49 and in the direction of the second horizontal reference line $Z_0$ 50 are determined by the cooperation of the position sensor 25 and the at least one image detection element 270 and image processing unit 290. The vertical distance of the operating unit 200 in the direction of the vertical reference line $Y_0$ 53 from the reclining surface 99 is determined by means of the marking and distance detection element 35. The determination of the positions $P_{Oxz}$ 52 (FIG. 1), $P_{Oxyz}$ 58 (FIG. 1) and $PL_{xyz}$ 38 (FIG. 1) with the cooperation of the position sensor 25, marking and distance detection element 35, control unit 390, as well as control of the lighting modules 3 and controllable light sources 5 in the ceiling 1 of the room by means of the light control unit 7 (FIG. 1) and central control station 11 is carried out as described in connection with FIG. 1.

Figure 4:
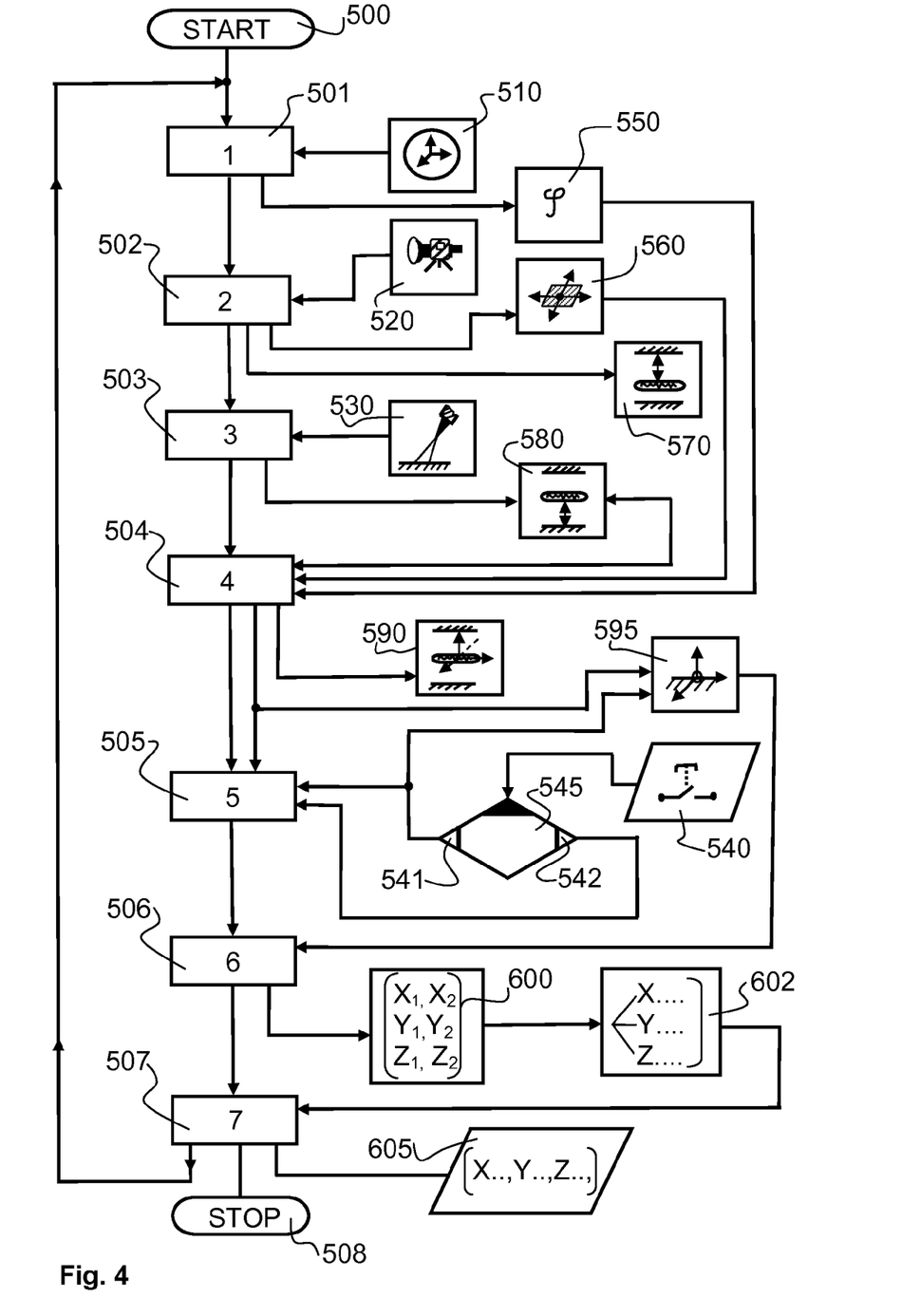
FIG. 4 is a flow chart of view showing a sequence of process steps for operating the medical lighting device.

FIG. 4 shows a view of a sequence of process steps for operating the medical lighting device according to FIGS. 1 through 3.

The continuous process with a sequence of seven steps begins immediately after the switching on 500 of the medical lighting device 1000 (FIG. 1) and is ended by switching off 508 the medical lighting device 1000 (FIG. 1).

A first data set 510 from the position sensor 25 (FIG. 1, FIG. 2, FIG. 3) is polled in a first step 501 in the operating unit 200 (FIG. 1, FIG. 2, FIG. 3) by the control unit 39 (FIG. 1, FIG. 2), and an angle data set ϕ 550 in relation to the vertical reference line is determined.

A second data set 520 from the image detection element 27 (FIG. 1, FIG. 2), 270 (FIG. 3) and the image processing unit 29 (FIG. 1, FIG. 2), 290 (FIG. 3) is polled in a second step 502 by the control unit 39 (FIG. 1, FIG. 2), 390 (FIG. 3), and a horizontal position 560 and a vertical distance 570 of the operating unit 200 (FIG. 1, FIG. 2, FIG. 3) from the ceiling 1 of the room (FIG. 1, FIG. 2, FIG. 3) is determined.

A third data set 530 from the marking and distance detection element 35 (FIG. 1, FIG. 2, FIG. 3) is polled in a third step 503 by the control unit 39 (FIG. 1, FIG. 2), and a vertical distance 580 from the reclining surface (FIG. 1, FIG. 2, FIG. 3) is determined.

A three-dimensional position 590 of the operating unit 200 (FIG. 1, FIG. 2, FIG. 3) is determined as a horizontal-vertical position $P_{Oxyz}$ 58 (FIG. 1) in the room in a fourth step 504 from the vertical distances 570, 580, the horizontal position 560 and the angle data set ϕ 550, and a three-dimensional position 595 of the light marking 37 (FIG. 1, FIG. 2, FIG. 3) on the reclining surface 99 (FIG. 1, FIG. 2, FIG. 3) is determined as a light marking position $PL_{xyz}$ 38 (FIG. 1).

A status of the operating element 33 (FIG. 1) is polled in a fifth step 505 as a third data set 540 by the control unit 39 (FIG. 1, FIG. 2) and sent to a decision unit 545. If the third data set 540 contains a positive confirmation 541, the three-dimensional position 595 of the light marking 37 (FIG. 1, FIG. 2, FIG. 3) on the reclining surface 99 (FIG. 1, FIG. 2, FIG. 3) is updated.

If the third data set 540 contains a negative confirmation 542, the three-dimensional position 595 on the light marking 37 (FIG. 1, FIG. 2, FIG. 3) on the reclining surface 99 (FIG. 1, FIG. 2, FIG. 3) is not updated and the previous three-dimensional position 595 on the light marking 37 (FIG. 1, FIG. 2, FIG. 3) on the reclining surface 99 (FIG. 1, FIG. 2, FIG. 3) remains valid.

The coordinates 600 of the illuminated area $X_{44}$ 71 (FIG. 1, FIG. 2, FIG. 3) are determined in a sixth step 506 in the central control station 11 (FIG. 1, FIG. 2, FIG. 3) on the reclining surface 99 (FIG. 1, FIG. 2, FIG. 3) and made available to the lighting control unit 7 (FIG. 1, FIG. 2, FIG. 3) as a coordinate data set 602.

The lighting control unit 7 (FIG. 1, FIG. 2, FIG. 3) converts the coordinate data set 602 into a control data set 605 in a seventh step and switches the controllable light sources 5 (FIG. 1, FIG. 2, FIG. 3) in the lighting modules 3 (FIG. 1, FIG. 2, FIG. 3) such that illumination of the selected illuminated area $X_{44}$ 71 (FIG. 1, FIG. 2, FIG. 3) on the reclining surface 99 (FIG. 1, FIG. 2, FIG. 3) is given.

The sequence of these seven steps 501 through 507 takes place continuously and, so to speak, simultaneously in a continual loop after switching on 500, and a decision 545 is made in the fifth step when actuating 540 the operating element 33 (FIG. 1) and a new coordinate data set 602 is generated in case of a positive confirmation 541, so that the illumination on the reclining surface 99 (FIG. 1, FIG. 2, FIG. 3) is updated.

While specific embodiments of the invention have been shown and described in detail to illustrate the application of the principles of the invention, it will be understood that the invention may be embodied otherwise without departing from such principles.

APPENDIX

List of Reference Numbers

1 Ceiling of room
3 Lighting module
5 Controllable light source
7 Lighting control unit
9 Lighting module control lines
11 Central control station
13 Coupling station
15 Station control line
17 First coupling element
19 Second coupling element
21 Data and supply cable
23 Housing
24 Power supply module
25 Position sensor 26 Communication module
27 Image detection element in/at the operating unit
28 Antenna
29 Image processing unit
31 Handle
33 Operating element
35 Marking and distance detection element
36 Light beam
37 Light marking
38 Light marking position $PL_{xyz}$
39 Control unit of the operating unit
41 Frame
43 Floor of room
45 First vertical distance $Y_1$
47 Second vertical distance $Y_2$
49 First horizontal reference line $X_0$
50 Second horizontal reference line $Z_0$
51 First angle $\phi_1$
52 Horizontal position $P_{0xz}$
53 Vertical reference line $Y_0$
55 Third vertical distance $Y_3$
57 Fourth vertical distance $Y_4$
58 Horizontal-vertical position $P_{0xyz}$
59 Orientation and orientation axis of the operating unit
61 Orienting light source at the operating unit
67 First reference element in/at the ceiling of the room
68 Third reference element in/at the ceiling of the room
69 Second reference element in/at the ceiling of the room
70 Right triangle
71 Illuminated area $X_{44}$
73 Marking area $X_{33}$
91 Second angle $\phi_2$
99 Reclining surface
100 Operating area light
200 Operating unit
270 Image detection elements in/at the ceiling of the room
271 Data lines
280 First arrangement of reference elements at the operating unit
288 Second arrangement of reference elements at the operating unit
290 Image processing unit in/at the ceiling of the room
300 Operating table
390 Control unit in the operating area light
301 Holding element
500-508 Sequence of process steps
510 First data set
520 Second data set
530 Third data set
540 Fourth data set
541 Positive confirmation
542 Negative confirmation
545 Decision
550 Angle data set cp
560 Horizontal position
570 Vertical distance from the ceiling of the room
580 Vertical distance from the reclining surface
590 Three-dimensional position of the operating unit in the room
595 Three-dimensional position of the light marking on the reclining surface
600 Coordinates of the illuminated area
602 Coordinate data set
605 Control data set
610 Orienting light source on the ceiling of the room
1000 Medical lighting device

What is claimed is:
1. A medical lighting device for illuminating an operating area in a space with a ceiling and a reclining surface, the medical lighting device comprising:
an operating area light comprising a lighting module comprising an arrangement with a controllable light source;
a central control station;
a lighting control unit;
a first reference element;
a second reference element;
a marking on the reclining surface;
a handheld operating unit comprising a position sensor generating position data comprising position information relating to a current position of the handheld operating unit, an image detection element, an image processing unit, a handle and an operating element arranged at the handle, the operating element comprising a physical feature actuated by a user at a location adjacent to or at the handle and generating operating element data corresponding to the actuation;
a marking and distance detection element generating a light beam for imaging the light marking on the reclining surface and detecting a vertical distance from the reclining surface to the handheld operating unit and sending vertical distance data;
a control unit to detect the position data of the position sensor and the operating element data of the operating element; and
a data transmission means for data transmission between the central control station, the lighting control unit and the control unit, wherein:
the image detection element, the reference elements, the image processing unit and the control unit cooperate to detect a vertical distance from the ceiling to the handheld operating unit in a direction of a vertical reference line;
the image detection element, the reference elements, the image processing unit and the control unit cooperate to detect a horizontal position of the operating unit in the space in a direction of a first horizontal reference line and in the direction of a second horizontal reference line, wherein the first reference element and the second reference element are arranged on the ceiling of the space;
the control unit determines an angle of the operating unit in a direction of the vertical reference line from measured data of the position sensor;
the central control station determines a horizontal-vertical position of the operating unit and a light marking position on the reclining surface from the vertical distance from the reclining surface, the vertical distance from the ceiling of the space, the horizontal position in the space and the at least one angle;
the control unit determines an illuminated area on the reclining surface from the light marking position on the reclining surface and the data of the operating element and sends results of the determination of the illuminated area to the central control station; and
the central control station and the lighting control unit actuate the operating area light such that the illuminated area determined is illuminated on the reclining surface.
2. The medical lighting device in accordance with claim 1, wherein the marking and distance detection element comprises a punctiform light source or as a punctiform laser light diode.
3. The medical lighting device in accordance with claim 1, wherein the position sensor comprises at least one of a three-axis acceleration sensor, a gyrometer, an inclinometer and a gyro sensor.

4. The medical lighting device in accordance with claim 1, wherein:
the marking and distance detection element is provided in or at the operating unit; and
the marking and distance detection element comprises an optical signal output.

5. The medical lighting device in accordance with claim 1, wherein:
the operating element provides an acoustic signal output.

6. The medical lighting device in accordance with claim 1, wherein an orienting light source at the operating unit is arranged on the ceiling of the space to light the first reference element and the second reference element.

7. A process for operating a medical lighting device, the process comprising the steps of:
providing a medical lighting device with a handheld operating unit having an image detection element, an image processing unit, a position sensor, a handle and an operating element and with a marking and distance detection element and with an operating area light with at least one lighting module having at least one controllable light source in a room with a ceiling and with a first reference element, a second reference element and a marking on a reclining surface wherein the first reference element and the second reference element are arranged on the ceiling of the room;
switching on the medical lighting device;
after switching on the lighting device continuously repeating a sequence of steps until a switching off of the medical lighting device, the sequence of steps comprising:
polling the position sensor and determining an angle data set relative to a vertical reference line;
polling the image detection element and the image processing unit and determining a horizontal position of the operating unit and a vertical distance of the operating unit from the ceiling;
polling the marking and distance detection element and determining a vertical distance from the reclining surface;
determining a three-dimensional position of the operating unit in the room as a horizontal-vertical position from the two vertical distances determined, the horizontal position determined and the angle data set determined, and determining a three-dimensional position of the light marking on the reclining surface as a light marking position;
polling a status of the operating element and updating the light marking position as a function of the status of the operating element;
determining coordinates of an illuminated area in a sixth step from the light marking position and providing the coordinates of an illuminated area as a coordinate data set; and
determining a control data set from the coordinate data set and actuating the controllable light source lighting module of the operating area light to provide illumination of the illuminated area determined on the reclining surface.

8. A process for operating a medical lighting device, the process comprising the steps of:
providing a medical lighting device for illuminating an operating area in a space with a ceiling and a reclining surface, the medical lighting device comprising an operating area light comprising a lighting module comprising an arrangement with a controllable light source, a central control station, a lighting control unit, an image detection element, an image processing unit, a first reference element, a second reference element, a marking on the reclining surface, a handheld operating unit with a position sensor, a handle and an operating element arranged at the handle, a marking and distance detection element generating a light beam for imaging the light marking on the reclining surface and detecting a vertical distance from the reclining surface and sending vertical distance data to the control unit, a control unit to detect data of the position sensor and data of the operating element, data transmission means for data transmission between the central control station, the lighting control unit and the control unit;
detecting a vertical distance from the ceiling in a direction of a vertical reference line with the image detection element, the reference elements, the image processing unit and the control unit cooperate;
detecting a horizontal position of the operating unit in the space in a direction of a first horizontal reference line and in the direction of a second horizontal reference line with the image detection element, the reference elements, the image processing unit and the control unit wherein the first reference element and the second reference element are arranged on the ceiling of the space and the image detection element and the image processing unit are arranged in/at the operating unit;
determining an angle of the operating unit in a direction of the vertical reference line from measured data of the position sensor with the control unit;
determining a horizontal-vertical position of the operating unit and a light marking position on the reclining surface from the vertical distance from the reclining surface, the vertical distance from the ceiling of the space, the horizontal position in the space and the at least one angle with the central control station;
determining an illuminated area on the reclining surface from the light marking position on the reclining surface and the data of the operating element with the control unit and sending results of the determination of the illuminated area to the central control station; and
actuating the operating area light with the central control station and the lighting control unit such that the illuminated area determined is illuminated on the reclining surface.

9. The process in accordance with claim 8, wherein the marking and distance detection element comprises a punctiform light source or as a punctiform laser light diode.

10. The process in accordance with claim 8, wherein the position sensor comprises at least one of a three-axis acceleration sensor, a gyrometer, an inclinometer and a gyro sensor.

11. The process in accordance with claim 8, wherein:
the marking and distance detection element is provided in or at the operating unit; and
the marking and distance detection element comprises an optical signal output.

12. The process in accordance with claim 8, wherein:
the operating element provides an acoustic signal output.

13. The process in accordance with claim 8, wherein an orienting light source at the operating unit is arranged on the ceiling of the space to light the first reference element and the second reference element.

* * * * *